| United States Patent [19] | [11] Patent Number: 4,717,769 |
| Sato et al. | [45] Date of Patent: Jan. 5, 1988 |

[54] PRODUCTION OF EPSILON-CAPROLACTAM

[75] Inventors: Hiroshi Sato; Kenichi Hirose; Masaru Kitamura; Youichi Umada, all of Osaka; Norio Ishii, Ehime; Hideto Tojima, Kyoto, all of Japan

[73] Assignee: Sumitomo Chemical Co., Ltd., Osaka, Japan

[21] Appl. No.: 19,851

[22] Filed: Feb. 27, 1987

[30] Foreign Application Priority Data

Apr. 21, 1986 [JP] Japan ................................. 61-91596

[51] Int. Cl.$^4$ .......................................... C07D 201/04
[52] U.S. Cl. ..................................... 540/536; 540/535
[58] Field of Search ................................. 540/535, 536

[56] References Cited

U.S. PATENT DOCUMENTS 4,359,421 11/1982 Bell et al. ............................. 340/535
4,472,516 9/1984 Frenken ................................. 502/60

OTHER PUBLICATIONS

Dokl. Akad. Nauk, 29 BSSR No. 10, pp. 924–927 (1985).

Primary Examiner—Robert T. Bond
Attorney, Agent, or Firm—Cushman, Darby & Cushman

[57] ABSTRACT $\epsilon$-caprolactam is produced by gas phase catalytic synthesis with high selectivity of lactam wherein cyclohexanone oxime is brought into contact with a crystalline metallo-silicate catalyst having Si/metal atomic ratio is more than 500. The metal moiety in the catalyst is Ga, Fe, B, Zr, Bi, Nb, Zn, Be, Cr, La, Ti, Hf, V and/or Cu.

10 Claims, No Drawings

PRODUCTION OF EPSILON-CAPROLACTAM

This invention relates to production of ε-caprolactam, more particularly, the use of a specific crystalline metallo silicate catalyst in production of ε-caprolactam from cyclohexanone oxime.

ε-caprolactam is an important material for nylon and the like. One of processes for preparing said caprolactam is liquid-phase catalytic rearrangement of cyclohexanone oxime in the presence of sulfuric acid. Alternatively, gas-phase catalytic rearrangements in the presence of solid acid are proposed, e.g., boric acid compounds (Japanese published unexamined patent application Nos. 37686/1978 and 12125/1971), silica-alumina (British Pat. No. 881927), solid phosphoric acid (British Pat. No. 881926), mixed metal oxides (Journal of the Chemical Society of Japan, No. 1, 77, 1977), Y-zeolite (Journal of Catalysis, 6, 247, 1966) and crystalline alumino-silicate (Japanese published unexamined patent application No. 139062/1982).

Problems encountered are use of a large amount of fuming sulfuric acid, a large amount of ammonium sulfate by-produced and corrossion of apparatuses caused by fuming sulfuric acid, when sulfuric acid is used above. One of approaches to dissolve the problems is the use of solid catalysts above. However, all of these processes are not satisfactory in respect of reaction selectivity of ε-caprolactam, life of catalyst, production yield per catalyst, conversion rate of oxime, etc. For instance, Japanese published unexamined patent application No. 139062/1982 where crystalline aluminosilicate e.g. ZSM-5 having 40–60 of Si/Al atomic ratio is used discloses that conversion rate of cyclohexanone oxime is said to be quantitative, but no selectivity of εcaprolactam is given and weight hourly space velocity (hereinafter referred to as "WHSV") is remarkably as low as about 2.5 hr$^{-1}$ and life of catalyst is as short as 15–20 hours. The present inventors have repeated the process of the Japanese published unexamined patent application mentioned above using the ZSM zeolite catalyst having the same Si/Al atomic ratio as above to confirm shortness of life of catalyst and low selectivity of ε-caprolactam, particularly too short life of catalyst and too small selectivity under commercial WHSV, for example, about 10 hr$^{-1}$ or higher.

The present inventors have studied production of ε-caprolactam using various crystalline metallo-silicate catalysts until it is found that a metallo-silicate having specific Si/metal atomic ratio greatly improves conversion rate of oxime, selectivity of lactam, life of catalyst, and productivity.

According to the present invention, in production of ε-caprolactam by gas-phase catalytic rearrangement of cyclohexanone oxime in the presence of crystalline metallo-silicate, an improvement in the crystalline catalyst is provided wherein Si/metal atomic ratio in crystal skeleton is not smaller than 500 excluding alumino-silicate.

The crystalline metallo-silicate is crystalline zeolite compound having at least one metal element as a constituent in crystal skeleton, said metal being selected from Ga, Fe, B, Zn, Cr, Be, Co, La, Ti, Zr, Hf, V, Ni, Sb, Bi, Cu and Nb. More specifically, mention may be made of, for example, gallosilicate, ferrosilicate, borosilicate, zinc silicate, chrome silicate, beryllium silicate, cobalt silicate, lanthanum silicate, titanium silicate, zirconium silicate, hafnium silicate, vanadium silicate, nickel silicate, antimony silicate, bismuth silicate, copper silicate and niobium silicate. There are many crystal forms in these metallo-silicates but pentasil form is preferable.

Atomic ratio in crystal skeleton is able to easily determine by technique familiar to the skilled in the art, e.g. atomic absorption spectroscopy, X-ray fluorecence spectroscopy. Si/metal atomic ratio should be at least 500. Crystalline metallo-silicate having such high silica content facilitates reaction, particularly selectivity of ε-caprolactam and life of catalyst.

External surface area of the metallo-silicate is another factor to give an influence to reaction. Metallo-silicate having external surface area of 5 m$^2$/g or more is preferred, because conversion to lactam and life of catalyst as well as catalytic activity or conversion rate of oxime are improved. Such metallosilicate has primary crystal particle size of as small as less than 0.5$\mu$ under a scanning electron microscope. The crystal particle size is assumed to facilitate increases in external surface area and reaction yield. The external surface area is observed by a porefilling up process, i.e., pores in crystal are filled up with organic or inorganic molecules and then the necessary surface area is observed by BET method on the basis of an adsorption amount of nitrogen or krypton adsorbed onto the external surface. The molecules to fill up the pore are organic ones such as butane, hexane, benzene and the like, water (7th and 8th Seminors on catalysts, Catalyst Society, Japan, 1984 and 1985) and organic amines, tetra-alkylammonium cation used as a crystallization-controlling agent in hydrothermal synthesis. For example, hydrothermal synthesis of crystalline metallo-silicate is effected in the presence of, usually, organic amines or tetra-alkylammonium cation as a crystallization-controlling agent which exists in a filler for pores just when the synthesis is finished. BET surface area of zeolite is external surface area, said zeolite having been dried at a temperature up to 120° C. immediately after the synthesis is finished.

The crystalline metallo-silicate catalyst may be selected from crystalline ones prepared by processes for example disclosed in J. of Molecular Catalysis, 31, 355–370 (1985), Japanese published unexamined patent application Nos. 7598/1980 and 32719/1985.

A Si-source material for preparing the present catalyst should be as pure as possible having as small as possible of Al impurity, e.g., tetraalkyl silicate, aerogel, colloidal silica, sodium silicate (JIS Grade No. 3 of water glass). Another metal source material is oxide, hydroxide, alkoxy derivative, nitrate or acetate of Ga, Fe, B, Zn, Be, Cr, Co, Ti, La, Zr, Hf, V, Ni, Sb, Bi, Cu or Nb.

Crystalline metallo-silicate obtained from hydrothermal synthesis should be calcined in air until organic amine cation is removed, subjected to ion-exchange with aqueous ammonium chloride solution or diluted aqueous hydrochloric acid solution and calcined again until it is converted to the H+ form, since the silicate usually contains organic amine cation used as a crystallization-controlling agent and alkali metal cations such as Na+, K+, etc. Alternatively, the corresponding polyvalent metal ion form may be used in place of the H+ form, wherein the ion-exchange is effected by use of aqueous alkaline earth metal solution containing, for example, $Ca^{2+}$, $Mg^{2+}$, $Sr^{2+}$ and $Ba^{2+}$, or aqueous lanthanoide series solution containing, for example, $La^{2+}$ and $Ce^{3+}$ in place of the aqueous ammonium chloride or diluted hydrochloric acid solution.

The present reaction is carried out in a manner of gas phase catalytic reaction in a fixed-bed or flow-layer operation. Cyclohexanone oxime, the starting compound, is vaporized in a vaporizer and then is brought in the gas form into contact with a catalyst. The cyclohexanone oxime may be fed alone, but preferably in the form of solution in benzene or toluene to the vaporizer. In the latter case, the solution may be carried by an inert carrier gas such as $N_2$, $CO_2$ etc., although the carrier gas is not always necessary. Preferred is $CO_2$ gas, since selectivity of lactam is improved.

Rearrangement reaction temperature is usually 250°–500° C., preferably 300°–450° C. Feeding speed (WHSV) is 0.1–100 $hr^{-1}$, preferably 1–50 $hr^{-1}$, more preferably 5–40 $hr^{-1}$.

Regeneration of catalyst whose activity falls down after a long use is effected by calcining at 450°–550° C. in air stream.

Isolation of ε-caprolactam is effected by, for example, cooling and condensing a reaction gas and then distilling or recrystallizing.

In accordance with the present process, conversion rate of cyclohexanone oxime and selectivity of ε-caprolactam are greatly improved, an amount of carbon deposition on a catalyst is very small, life of catalyst is greatly prolonged and high yield of ε-caprolactam is secured for a long period of time. That is to say, good balance is maintained among activity, selectivity and life which are important factors for catalysts from an economical point of view. Furthermore, high productivity per catalyst is attained with high WHSV. Recovery of activity is easily made by calcining a used catalyst in air. Repeated use of catalyst is possible.

REFERENCE EXAMPLE 1

(Synthesis of high silica gallosilicate)

Highly pure "Aerozil" (trade name, manufactured by Japan Aerozil Co. Ltd., Al ≦8.8 ppm, 70 g), distilled water (600 g), aqueous solution (150 g) containing tetra-n-propylammonium bromide (34 g) and gallium nitrate (0.488 g) were charged in an autoclave (1.5 l) made of stainless steel and the content was vigorously stirred. Aqueous solution (100 ml) containing sodium hydroxide (7.4 g) was charged at one time and the mixture was vigorously stirred for 30 min. The gel solution had pH of 12.8. The autoclave was tightly sealed, and then inner temperature was raised up to 190° C. Stirring (400 r.p.m.) was continued for 50 hours to carry out hydrothermal synthesis keeping the temperature as above. PH at the end of the hydrothermal synthesis was 11.66. White solid produced was separated by filtration. Product was continuously washed with distilled water until pH of filtrate reached about 7. Product was dried at 120° C. for 16 hours. BET surface of crystal at that stage was observed by a nitrogen gas adsorption method to obtain 1.9 $m^2/g$ of external surface area.

The crystal dried was calcined in air stream at 500°–550° C. for 4 hours to obtain 70 g of powdery white crystals which were identified as crystalline gallosilicate similar to ZSM-5, so far as crystal form is concerned (powder X-ray diffraction assay). Si/Ga atomic ratio =890 (atomic absorption spectroscopy assay.)

To the crystals (10 g) was added 5% aqueous $NH_4Cl$ solution (100 g) and then the mixture was subjected to ion-exchange at 50–60° C. for one hour before filtration. The ion-exchange treatment was repeated four times. Crystals were washed with distilled water until no $Cl^+$ was detected. Crystals were dried at 120° C. for 16 hours. Crystals ($NH_4$-form) were shaped to particles (24–48 mesh in size) and calcined at 500° C. for 4 hours to obtain gallosilicate (H-form). Surface acidity (pKa) was −3 (an indicator assay). Acid amount of external surface at 350° C. was 4.87μ equivalent/g on the basis of an adsorption amount of 4-methylquinoline (which is referred to as 4MQ hereinafter).

EXAMPLE 1 (A CATALYTIC ACTIVITY TEST UNDER FIXED BED GASEOUS REACTION)

Gallosilicate catalyst (H-form, 0.6 g, 1.04 ml, 24–48 mesh in size), prepared in Reference example 1 above was packed in a reactor made of quartz (32 cm long, 1 cm inner diameter) and pre-heating was effected by flowing $N_2$ gas at 350° C. for one hour. Cyclohexanone oxime (8.0 wt. %)/benzene solution was fed (WHSV=11.7 $hr^{-1}$) from vaporizer. Temperature of the catalyst layer was 350° C. Reaction product was trapped and collected under water-cooling. Gas-chromatography [column: 20% silicone SE-30/chromosorb AW-DMCS (60/80 M) 2 m: glass column, internal standard pseudocumene] gave the result shown in Table 1.

TABLE 1

| time elapsed (hr) | cyclohexanone oxime conversion (%) | ε-caprolactam yield (%) | ε-caprolactam selectivity (%) |
|---|---|---|---|
| 1.3 | 94.6 | 61.9 | 65.5 |
| 2.3 | 88.7 | 64.0 | 72.2 |
| 3.3 | 84.5 | 62.5 | 74.0 |
| 4.3 | 81.4 | 59.4 | 73.0 |
| 5.3 | 78.0 | 59.5 | 76.8 |
| 6.3 | 76.0 | 56.7 | 74.6 |
| 7.3 | 73.2 | 57.0 | 77.8 |
| 8.3 | 71.1 | 56.0 | 78.6 |
| 9.3 | 70.0 | 55.3 | 79.0 |
| 10.3 | 69.6 | 54.6 | 78.5 |
| 11.3 | 68.8 | 55.0 | 80.0 |
| 12.3 | 68.5 | 54.5 | 79.5 |

REFERENCE EXAMPLE 2
(SYNTHESIS OF HIGH SILICA GALLOSILICATE)

Highly pure tetraethyl ortho-silicate (Al≦10 ppm, 100 g) and aqueous solution (217.5 g) containing 10% tetra-n-propylammonium hydroxide were charged in an autoclave (1.5 l) made of stainless steel, and the content was vigorously stirred. Solution (214 g) of gallium nitrate in ethylene glycol [Ga(NO$_3$)$_3$:100 mg] was added and the mixture was vigorously stirred for 30 min. The solution had pH of 12.5. The autoclave was tightly sealed and inner temperature was raised up to 105° C. Stirring (400 r.p.m.) was continued for 120 hours at that temperature to carry out hydrothermal synthesis. Pressure in the autoclave was raised to 2-2.5 kg/cm$^2$. PH at the end of the hydrothermal synthesis was 11.88.

Filtration, washing and drying were applied in accordance with the latter part of Reference example 1 to obtain crystals (BET surface=9.3 m$^2$/g in terms of external surface area). The crystals were further calcined in air stream at 500°-550° C. for four hours to obtain powdery white crystals (28 g) which were identified as crystalline gallosilicate similar to ZSM-5 (powder X-ray diffraction assay). Si/Ga atomic ratio=2030 (atomic absorption spectroscopy assay).

Ion exchange treatment with NH$_4$Cl, washing and calcination were effected in the same way as in Reference example 1 to obtain H-form gallosilicate. Surface acidity (pKa) = −3.0 (an indicator assay). Acid amount of external surface =3.9μ equivalent/g (4 MQ).

EXAMPLE 2

Example 1 was repeated except that a catalyst used was crystalline gallosilicate (H-form, 24-48 mesh in size) prepared by Reference example 2 in place of the gallosilicate in Example 1.

Result is shown in Table 2.

TABLE 2

| time elapsed (hr) | cyclohexanone oxime conversion (%) | ε-caprolactam yield (%) | ε-caprolactam selectivity (%) |
|---|---|---|---|
| 1.3 | 100 | 76.5 | 76.5 |
| 2.3 | 100 | 80.0 | 80.0 |
| 3.3 | 100 | 81.1 | 81.1 |
| 4.3 | 100 | 80.4 | 80.4 |
| 5.3 | 100 | 81.1 | 81.1 |
| 6.3 | 100 | 82.2 | 82.2 |
| 7.3 | 100 | 80.6 | 80.6 |
| 8.3 | 100 | 80.3 | 80.3 |
| 9.5 | 100 | 82.6 | 82.6 |
| 10.5 | 100 | 84.5 | 84.5 |
| 11.5 | 100 | 83.2 | 83.2 |
| 13.5 | 100 | 84.4 | 84.4 |

REFERENCE EXAMPLE 3

Hydrothermal synthesis was carried out in accordance with Reference example 2 except that ferric chloride (anhydrous, 39 mg) was used in place of the gallium nitrate. Filtration, washing and drying gave crystals (BET surface=7.3 m$^2$/g in terms of external surface area). The crystals were calcined to obtain powdery white crystals (28 g) which were identified as crystalline ferrosilicate similar to ZSM-5 (powder X-ray diffraction assay). Si/Fe atomic ratio =1600 (atomic absorption spectroscopy assay).

Ion exchange treatment with NH$_4$Cl, washing and calcination were effected in accordance with Reference example 1 to obtain ferrosilicate (H-form). Surface acidity (pKa)= −3.0 (an indicator assay). Acid amount of external surface=about zero (4 MQ).

EXAMPLE 3

Rearrangement reaction was effected in accordance with Example 1 except that the crystalline ferrosilicate (H-form, 24-48 mesh in size) obtained in Reference example 3 was used in place of the gallosilicate.

Result is shown in Table 3.

TABLE 3

| time elapsed (hr) | cyclohexanone oxime conversion (%) | ε-caprolactam yield (%) | ε-caprolactam selectivity (%) |
|---|---|---|---|
| 1.3 | 100 | 82.0 | 82.0 |
| 2.3 | 100 | 82.2 | 82.2 |
| 3.3 | 100 | 82.8 | 82.8 |
| 4.3 | 100 | 81.8 | 81.8 |
| 6.3 | 100 | 82.1 | 82.1 |
| 8.3 | 100 | 83.9 | 83.9 |
| 9.3 | 100 | 83.5 | 83.5 |
| 11.3 | 100 | 83.5 | 83.5 |
| 12.3 | 100 | 84.2 | 84.2 |
| 13.3 | 100 | 82.4 | 82.4 |
| 14.3 | 100 | 82.8 | 82.8 |
| 15.3 | 100 | 83.5 | 83.5 |

EXAMPLE 4 (A REACTION UNDER HIGH WHSV)

Crystalline gallosilicate catalyst prepared by Reference example 1 (H-form, 24-48 mesh in size, 0.3 g, 0.5 ml) was packed in a quartz reactor (82 cm long, 1 cm inner diameter) and preheating was effected by flowing N$_2$ gas at 350° C. for one hour. Cyclohexanone oxime (8 wt %)/benzene solution was fed (WHSV=38.5 hr$^{-1}$) from a vaporizer. Temperature of the catalyst bed was 350° C. Reaction product was trapped and collected under watercooling. Gas-chromatography gave the result shown in Table 4.

TABLE 4

| time elapsed (hr) | cyclohexanone oxime conversion (%) | ε-caprolactam yield (%) | ε-caprolactam selectivity (%) |
|---|---|---|---|
| 1.3 | 87.6 | 66.9 | 76.4 |
| 2.3 | 72.3 | 56.7 | 78.4 |
| 3.3 | 63.2 | 47.0 | 74.4 |
| 4.3 | 54.8 | 42.2 | 77.0 |
| 5.3 | 49.9 | 37.3 | 74.9 |
| 6.3 | 43.4 | 34.5 | 79.4 |
| 7.3 | 42.0 | 32.8 | 78.1 |

EXAMPLE 5

Rearragement reaction was carried out in accordance with Example 4 except that the crystalline gallosilicate prepared by Reference example 2 (H-form, 2.4-4.8 mesh in size) was used in place of the gallosilicate in Example 4.

Result is shown in Table 5.

TABLE 5

| time elapsed (hr) | cyclohexanone oxime conversion (%) | ε-caprolactam yield (%) | ε-caprolactam selectivity (%) |
|---|---|---|---|
| 1.3 | 99.8 | 82.1 | 82.3 |
| 2.3 | 99.1 | 85.0 | 85.8 |
| 3.3 | 97.6 | 84.5 | 86.6 |
| 4.3 | 94.7 | 81.7 | 86.3 |
| 5.3 | 93.2 | 78.7 | 84.4 |
| 6.3 | 90.5 | 79.3 | 87.6 |

REFERENCE EXAMPLE 4

Hydrothermal synthesis was carried out in accordance with Reference example 2 except cobalt (III) acetylacetonate [Co(AcAc)₃; 85 mg] was used in place of the gallium nitrate. Filtration, washing and drying gave crystals (BET surface=10.7 m²/g in terms of external surface area). The crystals were calcined to obtain powdery white crystals (28 g) which were identified as crystalline cobalt silicate similar to ZSM-5 (powder X-ray diffraction assay). Si/Co atomic ratio=1310 (atomic absorption spectroscopy assay).

Ion exchange treatment with NH₄Cl,4Cl, washing and calcination were effected in accordance with Reference example 1 to obtain cobalt silicate (H-form). Surface acidity (pKa)=+3.3 (an indicator assay). Acid amount of external surface=2.5μ equivalent/g (4MQ).

EXAMPLE 6

Rearrangement reaction was carried out in accordance with Example 4 except that the crystalline cobalt silicate obtained by Reference example 4 (H-form, 24–48 mesh in size) in place of the gallosilicate.

The result is shown in Table 6.

TABLE 6

| time elapsed (hr) | cyclohexanone oxime conversion (%) | ε-caprolactam yield (%) | ε-caprolactam selectivity (%) |
|---|---|---|---|
| 1.3 | 100 | 82.6 | 82.6 |
| 2.3 | 100 | 81.8 | 81.8 |
| 3.3 | 99.7 | 82.4 | 82.6 |
| 4.3 | 99.2 | 83.3 | 84.0 |
| 5.3 | 98.2 | 81.1 | 82.6 |
| 6.3 | 97.1 | 80.1 | 82.5 |

REFERENCE EXAMPLES 5–7

Hydrothermal synthesis, drying, calcination, ion exchange treatment with NH₄Cl, drying and calcination were repeated as in Reference example 1, except that amounts of gallium nitrate as in Table 7 were used in place of 0.488 g. Crystalline gallosilicates having various Si/Ga atomic ratios were obtained as in Table 7.

TABLE 7

| Reference example No. | Ga(NO₃)₂ feed (g) | Si/Ga atomic ratio in gallosilicate | surface area BET (m²/g) | acid amount of external surface (μeq./g) | surface acidity (Ho) |
|---|---|---|---|---|---|
| 5 | 0.135 | 3,490 | 2.2 | 1.20 | −3.0 |
| 6 | 0.97 | 450 | 2.0 | 6.41 | −3.0 |
| 7 | 8.78 | 50 | 2.5 | 22.8 | −5.6 |

EXAMPLE 7

Rearrangement reaction was carried out in accordance with Example 4 except that the gallosilicate produced by Reference example 5 (H-form, 24–48 mesh in size) was used in place of the gallosilicate in Example 4. Result is shown in Table 8.

TABLE 8

| time elapsed (hr) | cyclohexanone oxime conversion (%) | ε-caprolactam yield (%) | ε-caprolactam selectivity (%) |
|---|---|---|---|
| 1.3 | 68.0 | 52.0 | 76.5 |
| 2.3 | 58.2 | 44.9 | 77.2 |
| 3.3 | 52.3 | 39.0 | 74.5 |
| 4.3 | 49.0 | 36.8 | 75.0 |
| 5.3 | 47.4 | 35.1 | 74.0 |
| 6.3 | 44.0 | 31.7 | 79.0 |
| 7.3 | 44.0 | 34.5 | 78.5 |

REFERENCE EXAMPLE 8

Hydrothermal synthesis, drying, calcination, on exchange treatment with NH₄Cl, and calcination were repeated as in Reference example 1 except that aluminium sulfate [Al₂(SO₄)₃.16H₂O; 0.68 g] was used in place of the gallium nitrate to obtain crystalline aluminosilicate zeolite (H-form, ZSM-5, Si/Al atomic ratio=49.2).

COMPARISON EXAMPLE 1

Rearrangement reaction was carried out in accordance with Example 4 except that crystalline aluminosilicate produced by Reference example 8 (H-form, ZSM-5, 24–48 mesh in size) was used in place of the gallosilicate.

Result is shown in Table 9.

TABLE 9

| time elapsed (hr) | cyclohexanone oxime conversion (%) | ε-caprolactam yield (%) | ε-caprolactam selectivity (%) |
|---|---|---|---|
| 1.3 | 68.5 | 34.3 | 50.1 |
| 2.3 | 24.1 | 13.2 | 53.4 |
| 3.3 | 14.3 | 7.7 | 53.8 |

COMPARISON EXAMPLE 2

Rearrangement reaction was carried out in accordance with Example 4 except that crystalline gallosilicate obtained in Reference example 6 (H-form, 24–48 mesh in size, Si/Ga atomic ratio : 450) was used in place of the gallosilicate in Example 4.

Result is shown in Table 10.

TABLE 10

| time elapsed (hr) | cyclohexanone oxime conversion (%) | ε-caprolactam yield (%) | ε-caprolactam selectivity (%) |
|---|---|---|---|
| 1.3 | 44.0 | 24.5 | 55.8 |
| 2.3 | 36.2 | 22.8 | 63.0 |
| 3.3 | 32.7 | 21.2 | 64.8 |
| 4.3 | 30.0 | 20.3 | 67.6 |
| 5.3 | 28.3 | 19.1 | 67.4 |

TABLE 10-continued

| time elapsed (hr) | cyclohexanone oxime conversion (%) | ε-caprolactam yield (%) | selectivity (%) |
|---|---|---|---|
| 6.3 | 28.0 | 18.5 | 66.0 |
| 7.3 | 26.9 | 17.5 | 65.2 |

COMPARISON EXAMPLE 3

Rearrangement reaction was carried out in accordance with Example 4 except that crystalline gallosilicate obtained in Reference example 7 (H-form, 24–48 mesh, Si/Ga atomic ratio: 50) in place of the gallosilicate in Example 4. Result is shown in Table 11.

TABLE 11

| time elapsed (hr) | cyclohexanone oxime conversion (%) | ε-caprolactam yield (%) | selectivity (%) |
|---|---|---|---|
| 1.3 | 58.5 | 26.3 | 45.0 |
| 2.3 | 40.0 | 16.3 | 40.7 |
| 3.3 | 35.3 | 12.8 | 36.0 |
| 4.3 | 28.5 | 10.1 | 35.4 |

REFERENCE EXAMPLE 9

Aqueous 10% tetra-n-propylammonium hydroxide solution (217.5 g), ethanol (214 g), aqueous niobium oxide-$NH_3$ complex (107.5 mg) solution (2 ml), highly pure tetraethyl ortho-silicate (Al <10 ppm, 100 g) were fed in this order to an autoclave (1.5 l) made of stainless steel and the content was stirred for one hour. The solution had pH of about 12.5. The autoclave was sealed tightly and stirring (more than 400 r.p.m.) was made at 105° C. for 48 hours to carry out hydrothermal synthesis. Pressure reached about 2.5 Kg/cm$^3$.

After the reaction was over, filtration, washing and drying were effected in accordance with Reference example 1 to obtain crystals whose BET surface area was 10.0 m$^2$/g in terms of external surface area. The crystals were further calcined in air stream at 500°–550° C. for four hours to obtain powdery white crystals (28.4 g) which were identified as crystalline niobium silicate similar to ZSM-5 (powder X-ray diffraction assay). Si/Nb atomic ratio=2964 (atomic absorption spectroscopy assay).

Ion exchange treatment, washing and calcination were applied in accordance with Reference example 1 to obtain niobium silicate (H-form). Surface acidity (pKa)=1.5 (an indicator assay). Acid amount of external surface=1.97μ equivalent/g (4 MQ).

REFERENCE EXAMPLES 10–13

Various metallo-silicate catalysts were prepared in accordance with Reference example 9 except that compounds listed in Table 12 were used in place of the niobium oxide-$NH_3$ complex in Reference example 9. Similarity of crystals obtained to ZSM-5 were confirmed by X ray diffraction assay.

Result is shown in Table 12.

TABLE 12

| No. | Compound formula | amount (mg) | Si/Me atomic ratio in metallo-silicate | Surface area BET (m$^2$/g) | Acid amount of external surface (μeq./g) | Surface acidity (Ho) |
|---|---|---|---|---|---|---|
| 10 | $H_3BO_3$ | 14.8 | 3,020 | 15.0 | 1.08 | −3.0 |
| 11 | $Ga(NO_3)_3.9H_2O$ | 100.3 | 1,986 | 16.9 | 4.50 | +1.5 |
| 12 | $Bi(NO_3)_3.5H_2O$ | 113.0 | 2,170 | 15.6 | 1.07 | −3.0 |
| 13 | $ZrO(NO_3)_2.2H_2O$ | 64.2 | 2,410 | 17.0 | 0.45 | −3.0 |

EXAMPLES 8–12

Rearrangement reactions were carried out in accordance with Example 4 except that the crystalline metallo-silicates obtained by Reference examples 9–13 (H-form, 24–48 mesh in size) were used in place of the gallosilicate.

Results are shown in Tables 13–17.

TABLE 13

(Niobium silicate of Reference example 9)

| time elapsed (hr) | cyclohexanone oxime conversion (%) | ε-caprolactam yield (%) | selectivity (%) |
|---|---|---|---|
| 1.3 | 99.8 | 82.0 | 82.2 |
| 2.3 | 99.5 | 86.9 | 87.3 |
| 3.3 | 98.9 | 87.1 | 88.1 |
| 4.3 | 97.2 | 87.0 | 89.5 |
| 5.3 | 96.7 | 84.0 | 86.8 |
| 6.3 | 95.3 | 83.6 | 87.7 |

TABLE 14

(Borosilicate of Reference example 10)

| time elapsed (hr) | cyclohexanone oxime conversion (%) | ε-caprolactam yield (%) | selectivity (%) |
|---|---|---|---|
| 1.3 | 100 | 82.4 | 82.4 |
| 2.3 | 99.7 | 84.7 | 85.0 |
| 3.3 | 99.3 | 85.7 | 86.3 |
| 4.3 | 98.8 | 83.7 | 84.7 |
| 5.3 | 97.9 | 83.0 | 84.8 |
| 6.3 | 97.0 | 83.0 | 85.5 |

TABLE 15

(Gallosilicate of Reference example 11)

| time elapsed (hr) | cyclohexanone oxime conversion (%) | ε-caprolactam yield (%) | selectivity (%) |
|---|---|---|---|
| 1.3 | 99.7 | 81.7 | 81.9 |
| 2.3 | 99.2 | 81.4 | 82.1 |
| 3.3 | 98.4 | 82.2 | 83.5 |
| 4.3 | 97.4 | 82.5 | 84.7 |
| 5.3 | 95.9 | 84.2 | 87.8 |
| 6.3 | 95.0 | 80.0 | 84.2 |

TABLE 16

(Bismuth silicate of Reference example 12)

| time elapsed (hr) | cyclohexanone oxime conversion (%) | ε-caprolactam yield (%) | selectivity (%) |
|---|---|---|---|
| 1.3 | 99.3 | 79.5 | 80.1 |
| 2.3 | 98.3 | 80.3 | 81.7 |

TABLE 16-continued (Bismuth silicate of Reference example 12)

| time elapsed (hr) | cyclohexanone oxime conversion (%) | ε-caprolactam yield (%) | ε-caprolactam selectivity (%) |
|---|---|---|---|
| 3.3 | 97.1 | 80.4 | 82.8 |
| 4.3 | 95.0 | 79.9 | 84.1 |
| 5.3 | 94.7 | 79.1 | 83.5 |
| 6.3 | 93.6 | 78.6 | 84.0 |

TABLE 17

(Zirconosilicate of Reference example 13)

| time elapsed (hr) | cyclohexanone oxime conversion (%) | ε-caprolactam yield (%) | ε-caprolactam selectivity (%) |
|---|---|---|---|
| 1.3 | 100 | 82.9 | 82.9 |
| 2.3 | 100 | 84.1 | 84.1 |
| 3.3 | 99.7 | 83.6 | 83.9 |
| 4.3 | 99.4 | 86.6 | 87.1 |
| 5.3 | 98.9 | 86.6 | 87.6 |
| 6.3 | 98.3 | 86.7 | 88.2 |

We claim:

1. A process for preparing ε-caprolactam which comprises bringing cyclohexanone oxime in a gaseous phase into contact with a crystalline metallo-silicate catalyst having Si/metal atomic ratio of 500 or more in crystal skeleton, excluding Al as the metal.

2. A process according to claim 1 wherein the catalyst has external surface area of 5 m$^2$/g or more.

3. A process according to claim 1 wherein the catalyst has external acid amount of not more than 5μ equivalent/g in terms of an absorption amount of 4-methylquinoline at 350° C.

4. A process according to claim 1 wherein the metal moiety of the catalyst is at least one selected from Ga, Fe, B, Zr, Bi, Nb, Zn, Be, Cr, La, Ti, Hf, V and Cu.

5. A process according to claim 1 wherein the catalyst has crystal form similar to ZSM-5.

6. A process according to claim 1 wherein the cyclonhexanone oxime is fed in the form diluted with benzene or toluene.

7. A process according to claim 1 wherein the cyclohexanone oxime is charged with WHSV of 1–50 hr$^{-1}$.

8. A process according to claim 7 wherein WHSV is 5–40 hr$_{-1}$.

9. A process according to claim 1 wherein the cyclohexanone oxime is charged in the form carried with inert gas.

10. A process according to claim 1 wherein the reaction is carried out at a temperature of 300–450° C.

* * * * *